United States Patent
Lin et al.

(10) Patent No.: US 9,993,445 B1
(45) Date of Patent: *Jun. 12, 2018

(54) ORAL SOLUTION COMPRISING ATOMOXETINE HYDROCHLORIDE AND METHODS THEREOF

(71) Applicant: TAHO Pharmaceuticals Ltd., Taipei (TW)

(72) Inventors: Chin Chung Lin, New Taipei (TW); Chien-Chiao Wang, New Taipei (TW); Catherine Lee, West Linn, OR (US)

(73) Assignee: TAHO PHARMACEUTICALS LTD., Taipei (TW)

(*) Notice: Subject to any disclaimer, the term of this patent is extended or adjusted under 35 U.S.C. 154(b) by 0 days. days.

This patent is subject to a terminal disclaimer.

(21) Appl. No.: 15/825,957

(22) Filed: Nov. 29, 2017

Related U.S. Application Data

(63) Continuation of application No. 15/379,142, filed on Dec. 14, 2016, now Pat. No. 9,855,228.

(51) Int. Cl.
| | |
|---|---|
| *A61K 31/138* | (2006.01) |
| *A61K 47/36* | (2006.01) |
| *A61K 9/00* | (2006.01) |
| *A61K 47/10* | (2017.01) |
| *A61K 9/08* | (2006.01) |
| *A61K 47/40* | (2006.01) |

(52) U.S. Cl.
CPC .......... *A61K 31/138* (2013.01); *A61K 9/0053* (2013.01); *A61K 9/08* (2013.01); *A61K 47/10* (2013.01); *A61K 47/36* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 5,011,688 | A | 4/1991 | Calam et al. |
| 5,891,801 | A | 4/1999 | Calam et al. |
| 6,042,812 | A | 3/2000 | Sanker et al. |
| 2002/0160982 | A1 | 10/2002 | Jacobs |
| 2003/0032600 | A1 | 2/2003 | Ulrich |
| 2010/0015184 | A1 | 1/2010 | Tuel |

FOREIGN PATENT DOCUMENTS

| | | | |
|---|---|---|---|
| EP | 3003384 B1 | | 10/2016 |
| WO | WO 2015/144255 | * | 10/2015 |
| WO | WO2015/144255 | | 10/2015 |

OTHER PUBLICATIONS

Weintraub et al. in Neurology, 75(5): 448-455 (2010) (Year: 2010).*
Berigan, T.R. in Primary Care Companion Journal of Clinical Psychiatry, 6(2): 93-94 (2004) (Year: 2004).*
Gadde et al. in International Journal of Obesity (London) 30(7): 1138-1142 (2006), Abstract (Year: 2006).*
International Search Report and Written Opinion in corresponding PCT Application No. PCTUS17/41937, dated Sep. 28, 2017.
Bhandari, V. et al. "Approaches of Taste Masking." International Journal of Pharmacy and Integrated Life Sciences, vol. 1, No. 5, 2013, pp. 48-61. ISSN : 2320-0782.
Bymaster, F. P. et al. "Atomoxetine Increases Extracellular Levels of Norepinephrine and Dopamine in Prefrontal Cortex of Rat: A Potential Mechanism for Efficacy in Attention Deficit/Hyperactivity Disorder." Neuropsychopharmacology, vol. 27, No. 5, Apr. 12, 2002, pp. 699-711.
Priya, Y. D. et al. "An Approach for Taste Masking of Bitter Drug Atomoxetine HCl." International Journal of Advances in Pharmaceutical Research, vol. 2, No. 4, 2011, pp. 119-121. ISSN: 2230-7583.
Nakano, M. et al. "Pharmacokinetic Profile and Palatability of Atomoxetine Oral Solution in Healthy Japanese Male Adults." Clin Drug Investig, vol. 36, Jul. 21, 2016, pp. 903-911. DOI:10.1007/s40261-016-0430-y.
Sohi, H. et al. "Taste Masking Technologies in Oral Pharmaceuticals: Recent Developments and Approaches." Drug Development and Industrial Pharmacy, 30:5, May 25, 2004, pp. 429-448. DOI: 10.1081/DDC-120037477.
Non-Final Office Action in corresponding U.S. Appl. No. 15/379,142 dated May 30, 2017.
Notice of Allowance in corresponding U.S. Appl. No. 15/379,142 dated Aug. 30, 2017.
Weintraub et al. in Neurology, 75(5): 448-455 (2010).
Berigan, T.R. in Primary Care Companion Journal of Clinical Psychiatry, 6(2): 93-94 (2004).
Gadde et al. in International Journal of Obesity (London) 30(7): 1138-1142 (2006), Abstract.
Sohi et al. in Drug Development and Industrial Pharmacy (30(5), 429-448 (2004).

* cited by examiner

*Primary Examiner* — Dennis Heyer
(74) *Attorney, Agent, or Firm* — Leason Ellis LLP

(57) ABSTRACT

Disclosed herein is an oral pharmaceutical composition in the form of an aqueous solution of atomoxetine as an active ingredient. The aqueous solution of atomoxetine comprises a taste-masked liquid carrier comprising peppermint, orange flavor and a viscosity agent. The combined flavors successfully masked atomoxetine hydrochloride's bitter smell and/or taste which makes it a novel palatable pharmaceutical composition. The viscosity agent improves the oral pharmaceutical composition's consistency and provides a smooth texture which makes it easy to swallow. More specifically, the oral pharmaceutical composition comprises effective amounts of: (a) atomoxetine or the pharmaceutically acceptable salts thereof; and (b) a taste-masked liquid carrier. Also provided is a method for making the aqueous solution of atomoxetine. The present disclosure also provides methods of using oral pharmaceutical composition for the treatment of a subject having a disorder treatable by the administration of atomoxetine. In one embodiment, the disorder is attention deficit hyperactivity disorder (ADHD).

18 Claims, No Drawings

ORAL SOLUTION COMPRISING ATOMOXETINE HYDROCHLORIDE AND METHODS THEREOF

CROSS REFERENCE TO RELATED APPLICATION

This application is a continuation application of U.S. application Ser. No. 15/379,142, filed Dec. 14, 2016. The entire disclosure of the above identified application is incorporated herein by reference in its entirety.

1. INTRODUCTION

Disclosed herein is an oral pharmaceutical composition in the form of a composition comprising atomoxetine as an active ingredient. The atomoxetine composition comprises a taste-masked liquid carrier comprising peppermint, orange flavor and a viscosity agent. The combined flavors successfully masked atomoxetine hydrochloride's bitter taste, numbing taste and after taste which makes it a novel palatable pharmaceutical composition. The viscosity agent improves the oral pharmaceutical composition's consistency and provides a smooth texture which makes it easy to swallow. More specifically, the oral pharmaceutical composition comprises effective amounts of: (a) atomoxetine or the pharmaceutically acceptable salts thereof; and (b) a taste-masked liquid carrier. Also provided is a method for making the atomoxetine composition. The present disclosure also provides methods of using oral pharmaceutical composition for the treatment of a subject having attention deficit hyperactivity disorder (ADHD). In particular, the oral pharmaceutical composition avoids swallow issue for children and elderly subjects.

2. BACKGROUND

Atomoxetine, (−)-N-methyl-3-phenyl-3 (o-tolyloxy) propylamine, or a pharmaceutically acceptable salt thereof, is a highly selective and potent inhibitor of the pre-synaptic noradrenaline transporter. Bymaster et al., 2002 Neuropsychopharmacology 27 (5): 699-711. The hydrogen chloride salt of atomoxetine, atomoxetine HCl, is marketed as Strattera®, which is prescribed as oral capsules for the treatment of attention deficit hyperactivity disorder (ADHD), in children, adolescents and adults. However, the solid dosage form has a potently bitter taste combined with a strong bitter aftertaste and a numbness that results in high incidence of non-compliance and ineffective therapy. Although there are many methods to suppress the bitterness reduce numbness and bitter aftertaste of drugs in general, they are not satisfactory to mask the highly bitter and sparingly water soluble drug such as atomoxetine. See, e.g., Vishani et al., 2013 International Journal of Pharmacy and Integrated Life Sciences 1(5): 48-61. An atomoxetine oral solution (4 mg/ml) is known to have been in the subject of a Bioequivalence study in healthy adult male Japanese subjects. Nakano et al., 2016 Clin Drug Investig. doi:10.1007/s40261-016-0430-y. Atomoxetine hydrochloride is soluble in water (27.8 mg/ml at room temperature), the desire for the development of a high concentrated oral solution dosage form of atomoxetine hydrochloride is complicated by the fact that it is an intensely bitter drug and it is even more unbearable at high concentration. Deepthi Priya et al., 2011 International Journal of Advances in Pharmaceutical Research, Vol. 2: 19. Modification with sweetening agent does not solve the bitterness and the prolonged aftertaste feeling of the patient taking the liquid dosage form. Instead, taste masking of atomoxetine solution in water utilizing certain taste masking excipients such as ethanol and mannitol is not effective because these agents only add to the bitter taste of atomoxetine, making the atomoxetine solution taste even worse. To complicate the matter further, high concentrations of taste masking agents such as sweeteners, sugar alcohols and/or flavors may be necessary for masking the taste of highly bitter drugs but such high quantities may decrease sharply the solubility of even readily soluble substances. Sohi et al., 2004 Drug Dev Ind Pharm 30(5):429-48. Taste Masking Technologies in Oral Pharmaceuticals: Recent Developments and Approaches.

Thus, it is a challenge to provide an acceptable palatable liquid dosage form, especially at high concentration of atomoxetine, for children and any individuals with any disorder that is treatable with atomoxtine who have actual or anticipated difficulties in swallowing the oral capsules or liquid formulation. In particular, the numbness of the tongue that is caused by ingesting atomoxetine has not been recognized or addressed by the industry. It remains as a challenge to provide an atomoxetine oral composition that is suitable for modifying, masking, reducing and/or suppressing unpleasant bitter taste, numbness of the tongue and the strong after-taste of atomoxetine. The present disclosure surprisingly provides pharmaceutical composition of oral aqueous atomoxetine solution at high concentration that effectively taste mask the prolonged bitterness, numbness and after taste caused by concentrated liquid dosage form.

3. SUMMARY

Atomoxetine caused bitter taste and after taste in patients that are administered with the drug. None of the existing formulations have taken into consideration of the numbness of the tongue and the oral cavity caused by oral administration of atomoxetine. It has been surprisingly found that a taste-masked liquid carrier for high concentration of atomoxetine comprising peppermint flavor, orange flavor and a viscosity agent provides a synergistic taste masking effect that reduces the bitter taste, the numbness of the tongue and the after taste. This masking effect could not be predicted from the taste masking effect of peppermint flavor, orange flavor and pullulan as individual agents. The liquid carrier functions in a slightly higher pH in the presently disclosed composition than other known Atomoxetine solutions. Other known atomoxetine HCL solutions are usually maintained at a lower pH, e.g., pH 4, which makes them easier to be preserved and more palatable. It is known that flavors that tasted desirable individually are not palatable when combined. Thus, it is surprising that the presently disclosed combination of flavors, sugars and viscosity agent provides effective taste masking without the commonly found undesirable taste in combination of flavors. In other words, the combination of these flavors and components was significantly more effective to mask the taste of atomoxetine than the additive effects using each of the components. In addition, the specific combination of the ingredients as disclosed herein achieves superior palatable results as compared to using other members in the whole class of each specific ingredient in general. For example, although most flavors are desirable individually, substituting a flavor with another desirable flavor has not resulted in an effective taste masking effect for atomoxetine. It has also been surprisingly revealed that the combination of certain sweeteners along with the combination of peppermint flavor, orange flavor and a viscosity agent provides a palatable atomoxetine pharmaceutical oral solution that taste like flavored soda and cools the tongue so the subject does not taste the bitterness, numbness or experience the after taste. The present disclosed composition reduces bitter taste, numbness and after taste that are associated with consuming a high concentration atomoxetine solution. The presently disclosed novel composition provides an easy to swallow, smooth mouthfeel which has minimal aftertaste.

The disclosed composition has synergistic taste masking effect which means a taste masking effect that is not merely additive, as would be predicted from the individual effect of each component, but which instead gives a level of taste masking above that which would be predicted, i.e., is synergistic. The oral pharmaceutical solutions of atomoxetine according to the present disclosure provide excellent taste masking effect while at the same time allow the optimal selection of concentration of taste masking components at the lowest feasible level.

In certain embodiments, the pharmaceutical compositions of atomoxetine may be free of additional polyhydric and sugar alcohols commonly used for the taste masking of oral liquid pharmaceutical compositions, such as glycerol, sorbitol and mannitol, which may raise additional safety and toxicity issues. Absence of additional polyhydric and sugar alcohols is important particularly in case of pediatric formulations.

In certain embodiments, the pharmaceutical compositions of atomoxetine disclosed herein may optionally contain additional ingredients commonly used in the preparation of oral liquid pharmaceutical compositions, such as antimicrobial preservatives, antioxidants, and viscosity agents.

Provided herein is a pharmaceutical composition comprising: (i) 0.5 mg/ml to 25 mg/ml of atomoxetine, and (ii) a carrier comprising: 0.01 mg/ml to 5 mg/ml peppermint flavor, 0.01 mg/ml to 10 mg/ml orange flavor, and 0.5 mg/ml to 600 mg/ml one or more sweeteners, wherein the pharmaceutical composition is a homogeneous oral solution, and wherein the pH of the composition is from 4 to 6.5

In one embodiment, the atomoxetine is atomoxetine hydrochloride.

In one embodiment, the solution is an aqueous solution.

In one embodiment, the concentration of atomoxetine is from 0.5 mg/ml to 25 mg/ml.

In one embodiment, the pharmaceutical composition further comprises 1 mg/ml to 300 mg/ml viscosity agent.

In one embodiment, the viscosity agent is pullulan, HPMC E15, HPMC E3, HPMC E6 or a combination thereof.

In one embodiment, the ratio of the peppermint flavor to orange flavor to sweetener is 1:3:100.

In one embodiment, the sweetener is sucralose or sucrose or a combination thereof.

In one embodiment, the concentration of the peppermint flavor is from 0.05 mg/ml to 5 mg/ml.

In one embodiment, the concentration of the orange flavor is from 0.01 mg/ml to 10 mg/ml.

In one embodiment, the pH is from 4 to 6.5. In one embodiment, the pH is from 5.5 to 6.5.

In one embodiment, the pharmaceutical composition is free of ethanol, sorbitol, and mannitol.

In one embodiment, the pharmaceutical composition further comprises glycerol and sulfobutylether-cyclodextrin ("SBE-β-CD").

In one embodiment, the peppermint is Kerry Peppermint or Wild peppermint. In certain embodiments, the peppermint is Natural Peppermint Flavor WONF #112136, WONF #FATEL649, WONF #FALT526, Kerry Ingredients And Flavors Italia Spa 58.3964.2P PHA Peppermint Flavor, 8.3748.UW PHA Peppermint Flavor, MANE: natural peppermint flavor F93554, and Mane Inc: Natural & Artificial peppermint flavor S.D. F93125, and or F94249 Peppermint Flavor.

Disclosed herein is a pharmaceutical composition which consists essentially of:
  1-10 mg/ml atomoxetine hydrochloride,
  50-100 mg/ml glycerol,
  50-100 mg/ml sweeteners,
  200-300 mg/ml SBE-β-CD,
  0.2-5 mg/ml peppermint flavor,
  0.1-10 mg/ml orange flavor, and
  0.5-10 mg/ml pullulan, and wherein the pH of the composition is from 4 to 6.5.

In one embodiment, the pH of the composition is from 5.5 to 6.5.

Disclosed herein is a method for treating a disorder comprising orally administering to a subject an effective amount of the pharmaceutical composition disclosed herein.

In one embodiment, the disorder is attention deficit hyperactivity disorder ("ADHD"), narcolepsy, depression, obesity, eating disorder, addiction, cognitive dysfunction and anxiety disorder.

In one embodiment, the disorder is ADHD.
In one embodiment, the subject is a human.
In one embodiment, the human is a child or an elderly.

4. DEFINITIONS

The term "synergistic effect" refers to the interaction between two or more components or chemicals when the combined effect is larger than the sum of the effects of the individual components.

The term "pharmaceutically acceptable salt" refers to any salt(s) of a compound provided herein which retains its biological properties and which is not toxic or otherwise undesirable for pharmaceutical use. Such salts may be derived from a variety of organic and inorganic counter-ions well known in the art.

The terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human.

The term "a subject in need thereof" refers to a subject diagnosed with ADHD. The subject may have been diagnosed with ADHD using standard medical techniques known to those of skill in the art. Alternatively a subject may exhibit one or more symptoms of ADHD.

The terms "compound", "agent" and "drug" are interchangeable.

The terms "therapeutic agent" and "therapeutic agents" refer to any agent(s) which can be used in the treatment of ADHD. In certain embodiments, the term "therapeutic agent" includes a compound provided herein. In one embodiment, a therapeutic agent is an agent which is known to be useful for, or has been or is currently being used for the treatment of ADHD.

The term "therapeutically effective amount" includes an amount of a compound or composition that, when administered to a subject for treating a disorder, is sufficient to effect such treatment. A "therapeutically effective amount" can vary depending on, inter alia, the symptoms and its severity, and the age, weight, etc., of the subject to be treated.

The term "treating" or "treatment" of a disorder refers, in one embodiment, to ameliorating the symptoms from the disorder that exists in a subject. In another embodiment, "treating" or "treatment" includes ameliorating at least one physical parameter, which may be indiscernible by the subject.

The term "about" refers to ±0.5 for a numerical value.

5. DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter. It is to be understood that particular features, structures, or characteristics described may be combined in various ways in one or more implementations.

5.1 Pharmaceutical Compositions

It has been surprisingly discovered that a taste-masked liquid carrier for high concentration of atomoxetine comprising peppermint flavor, orange flavor and a viscosity agent provides a synergistic taste masking effect that could not be predicted from the taste masking effect of peppermint flavor, orange flavor and pullulan as individual agents. The liquid carrier functions in a slightly higher pH in the presently disclosed composition than other known Atomoxetine solutions. Other known atomoxetine solutions are usually maintained at a lower pH, i.e., pH, 4 which makes them easier to be preserved and more palatable. It is known that flavors that tasted desirable individually are not palatable when combined. For example, combining any two flavors does not mean that the final combination would be more palatable. If the two flavors are not compatible with each, combining them may or may not make them more palatable. For example, blackcurrant flavor and cheery flavor might be palatable individually, but when combined, the combination is not as palatable. Thus, it is surprising that the presently disclosed combination of flavors, sugars and viscosity agent provides effective taste masking without the commonly found undesirable taste in combination of flavors. In other words, the combination of these flavors and components was significantly more effective to mask the taste of atomoxetine than the additive effects using each of the components. In addition, the specific combination of the ingredients as disclosed herein achieves superior palatable results as compared to using other members in the whole class of each specific ingredient in general. For example, although most flavors are desirable individually, substituting a flavor with another desirable flavor has not resulted in an effective taste masking effect for atomoxetine. It has also been surprisingly revealed that the combination of certain sweeteners along with the combination of peppermint flavor, orange flavor and pullulan provides a palatable atomoxetine pharmaceutical oral solution that taste like flavored soda and cools the tongue so the subject does not taste the bitterness or after taste in the tongue. The present disclosed composition reduces bitter after taste and numbness that are associated with high concentration atomoxetine solution. The presently disclosed novel composition provides an easy to swallow, smooth mouthfeel which has minimal aftertaste.

The disclosed composition has synergistic taste masking effect which means a taste masking effect that is not merely additive, as would be predicted from the individual effect of each component, but which instead gives a level of taste masking above that which would be predicted, i.e., is synergistic. The oral pharmaceutical solutions of atomoxetine according to the present disclosure provide excellent taste masking effect while at the same time allow the optimal selection of concentration of taste masking components at the lowest feasible level.

In certain embodiments, the pharmaceutical compositions of atomoxetine may be free of additional polyhydric and sugar alcohols commonly used for the taste masking of oral liquid pharmaceutical compositions, such as sorbitol and mannitol, which may raise additional safety and toxicity issues. Absence of additional polyhydric and sugar alcohols is important particularly in case of pediatric formulations.

In one embodiment, the oral pharmaceutical composition is in the form of an aqueous solution of atomoxetine as an active ingredient. In one embodiment, the oral pharmaceutical composition comprises atomoxetine as a solute that is completely dissolved when administered. In one embodiment, the oral pharmaceutical composition is not an oral suspension. The aqueous solution of atomoxetine comprises a taste-masked liquid carrier comprising peppermint, orange flavor and a viscosity agent. The combined flavors successfully masked atomoxetine hydrochloride's bitter taste and after taste which makes it a novel palatable pharmaceutical composition. The viscosity agent improves the oral pharmaceutical composition's consistency and provides a smooth texture which makes it easy to swallow. More specifically, the oral pharmaceutical composition comprises effective amounts of: (a) atomoxetine or the pharmaceutically acceptable salts thereof; and (b) a taste-masked liquid carrier. The pharmaceutical compositions disclosed herein can be formulated using methods available in the art and those disclosed herein.

In certain embodiments, the composition comprises about 0.5-3 mg/ml, about 3-5 mg/ml, about 5-8 mg/ml, about 8-10 mg/ml, about 10-12 mg/ml, about 12-15 mg/ml, about 15-18 mg/ml, about 18-20 mg/ml, about 20-23 mg/ml and about 23-25 mg/ml of atomoxetine and a carrier comprising: (i) about 0.05-0.1 mg/ml, about 0.1-0.5 mg/ml, about 0.5-1 mg/ml, about 1-3 mg/ml, about 3-5 mg/ml, about 5-8 mg/ml, and about 8-10 mg/ml peppermint flavor; (ii) about 0.01-0.05 mg/ml, about 0.05-0.1 mg/ml, about 0.1-0.5 mg/ml, about 0.5-1 mg/ml, about 1-3 mg/ml, about 3-5 mg/ml, about 5-8 mg/ml, about 8-10 mg/ml, about 10-15 mg/ml and about 15-20 mg/ml of orange flavor; and (iii) about 0.5-1 mg/ml, about 1-3 mg/ml, about 4 mg/ml, about 3-5 mg/ml, about 5-8 mg/ml, about 8-10 mg/ml, about 10-15 mg/ml, about 15-20 mg/ml, about 20-30 mg/ml, about 30-40 mg/ml, about 40-50 mg/ml, about 50-60 mg/ml, about 60-70 mg/ml, about 70-80 mg/ml, about 80-90 mg/ml, about 90-100 mg/ml, about 100-110 mg/ml, about 110-120 mg/ml, about 120-130 mg/ml, about 130-140 mg/ml, about 140-150 mg/ml, about 150-160 mg/ml, about 160-170 mg/ml, about 170-180 mg/ml, about 180-190 mg/ml, about 190-200 mg/ml, about 200-250 mg/ml, about 250-300 mg/ml, about 300-350 mg/ml, about 350-400 mg/ml, about 400-450 mg/ml, about 450-500 mg/ml, about 500-550 mg/ml, about 550-600 mg/ml of one or more sweeteners.

In one embodiment, the composition comprises 0.2 mg/ml to 5 mg/ml of peppermint flavor.

In one embodiment, the composition comprises 0.1 mg/ml to 10 mg/ml of orange flavor.

In certain embodiments, the composition does not comprises fruity flavor, blackberry flavor and/or raspberry flavor.

In certain embodiments, the composition comprises fruity flavor, blackberry flavor and/or raspberry flavor.

In certain embodiment, the pH of the composition is about 4-4.5, about 4.5-5, about 5-5.5, about 5.5-6, about 6-6.1, about 6.1-6.2, about 6.2-6.3, about 6.3-6.4, about 6.4-6.5, about 6.5-6.6.

In certain embodiments, the composition does not comprise xylitol and/or maltitol. In certain embodiments, the composition does not comprise ethanol, sorbitol, and mannitol.

In certain embodiments, the composition comprises xylitol and/or maltitol. In certain embodiments, the composition comprises ethanol, sorbitol, and mannitol.

In certain embodiments, the composition comprises glycerol and sulfobutylether-cyclodextrin ("SBE-β-CD"). In certain embodiments, the composition comprises about 50-60 mg/ml, about 60-70 mg/ml, about 70-80 mg/ml, about 80-90 mg/ml, about 90-100 mg/ml, about 100-110 mg/ml, about 110-120 mg/ml, about 120-130 mg/ml, about 130-140 mg/ml, about 140-150 mg/ml, about 150-160 mg/ml, about 160-170 mg/ml, about 170-180 mg/ml, about 180-190 mg/ml, about 190-200 mg/ml, about 200-250 mg/ml, about 250-300 mg/ml of SBE-β-CD.

In certain embodiments, the composition further comprises about 50-55 mg/ml, about 55-60 mg/ml, about 60-65 mg/ml, about 65-70 mg/ml, about 70-75 mg/ml, about 75-80 mg/ml, about 80-85 mg/ml, about 85-90 mg/ml, about 90-95 mg/ml, about 95-100 mg/ml of glycerol.

In certain embodiments, the composition further comprises about 1-3 mg/ml, about 3-5 mg/ml, about 5-8 mg/ml, about 8-10 mg/ml, about 10-15 mg/ml, about 15-20 mg/ml, about 20-30 mg/ml, about 30-40 mg/ml, about 40-50 mg/ml, about 50-60 mg/ml, about 60-70 mg/ml, about 70-80 mg/ml, about 80-90 mg/ml, about 90-100 mg/ml, about 100-110 mg/ml, about 110-120 mg/ml, about 120-130 mg/ml, about 130-140 mg/ml, about 140-150 mg/ml, about 150-160 mg/ml, about 160-170 mg/ml, about 170-180 mg/ml, about 180-190 mg/ml, about 190-200 mg/ml, about 200-250 mg/ml, about 250-300 mg/ml of viscosity agent.

In certain embodiments, the viscosity agent is pullulan, HPMC E15, HPMC E3, HPMC E6 or a combination thereof.

In certain embodiments, the sweetener is sucrose, sucralose or a combination thereof. In certain embodiments, the composition comprises about 10-20 mg/ml, about 20-30 mg/ml, about 30-40 mg/ml, about 40-50 mg/ml, about 50-60 mg/ml, about 60-70 mg/ml, about 70-75 mg/ml, about 75-80 mg/ml, about 80-90 mg/ml, about 90-100 mg/ml of sucrose. In certain embodiments, the composition comprises about 0.01-0.05 mg/ml, about 0.05-0.1 mg/ml, about 0.1-0.5 mg/ml, about 0.5-1 mg/ml, about 1-3 mg/ml, about 3-5 mg/ml, about 5-8 mg/ml, about 8-10 mg/ml, about 10-15 mg/ml and about 15-20 mg/ml of sucralose.

In certain embodiments, the ratio of the peppermint flavor to orange flavor to sweetener is about 1:3:100, about 1:4:100 or about 1:5:100.

A pharmaceutical composition which consists essentially of:
  1-10 mg/ml atomoxetine hydrochloride,
  50-100 mg/ml glycerol,
  50-100 mg/ml sweeteners,
  200-300 mg/ml SBE-β-CD,
  0.2-5 mg/ml peppermint flavor,
  0.1-10 mg/ml orange flavor, and
  0.5-10 mg/ml pullulan, and wherein the pH of the composition is from 4 to 6.5.

Flavoring agents include natural, artificial and synthetic flavor and flavoring aromatics and/or oils, oleoresins may be used. These flavoring agents may be used in liquid or solid form and may be used individually or in admixture.

Some useful artificial, natural and synthetic flavors such as lime, maple, Vanilla, Pear, Blackcurrant, almond, aniseed, apple, barley Sugar, chocolate, apricot, banana, honeycomb, blackberry, banana, blueberry, boysenberry, Fruit, tangerine & orange, butter caramel, cherry, fresh peach, Cola, Honey, Kiwifruit, Lemon, Guava Lime, Mango, orange, Nutmeg, Grapefruit, Passionfruit, Peppermint, pineapple, raspberry, peach, spearmint, strawberry, tropical fruit, wild berry, cranberry, apricot, lemon Myrtle, melon, mint, bubble gum, yoghurt, summer fruit, lychee, nectarine, watermelon, and French vanilla mixtures thereof and the like.

Flavor suppliers such as non-limiting representative of Abelei Inc, Ampacet Corp, Clariant Canada Inc, Dragoco Gerberding And Co Ag, Firmenich Inc, Flavor And Fragrance Specialties Inc, Flavors North America Inc, H Reisman Corp, J Manheimer Inc, Mastertaste Inc Dba Mastertaste Spa, Metarom Canada Inc, Milliken And Co, Perfumery Assoc Inc, Robertet Flavors Inc, Tastemaker, Warner Jenkinson Co, Am Todd Co, Anhui Worldbest Pharmaceutical Co Ltd, David Michael and Co Inc, Dragoco Riech Und Geschmack Stoffe Gmbh, Fona International Inc, Glidco Inc, Henry H Ottens Manufacturing Co Inc, Kerry Ingredients And Flavours Italia Spa, Mane Inc, Symrise Gbmh Co Kg, Symrise Inc, Talasago International Corp, Ungerer And Co, Wild Flavors Inc, WM Leman Inc., Wild Flavors Inc.

Compositions may be made, as liquid compositions for oral administration, of solutions which are pharmaceutically acceptable, suspensions, emulsions, syrups and elixirs containing inert diluents, such as water or liquid paraffin. The oral liquid pharmaceutical solution can comprises one or more pharmaceutically acceptable excipient which is selected from the group comprising co-solvents, solvents, antioxidants, microbial preservatives, buffering agents, aromatic agents, sweeteners and diluents. Co-solvents and solvents may include but not limited to glycerine, alcohols, propylene glycol, polyethylene glycol, benzyl alcohol, water, ethanol, isopropyl alcohol or their mixtures thereof. These compositions can also comprise substances other than diluents, for example wetting, sweetening or flavoring products. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier. Examples of suitable pharmaceutical carriers are described in "Remington's Pharmaceutical Sciences" by E. W. Martin. Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents. Oral Dosage Forms Pharmaceutical compositions that are suitable for oral administration can be presented as discrete liquid dosage forms. Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

5.2 Methods of Making the Atomoxetine Composition

The compositions of the present invention may be prepared using methods as exemplified below.

In one embodiment, water, preservatives, atomoxetine, sweetener, flavors, viscosity agent or complexation agent are mixed until all components are completely dissolved. The pH or the composition is then adjusted to about 4-6.5. The volume is adjusted to the final volume by further addition of water. The method does not require heating or cooling steps during the preparation.

In one embodiment, the method comprises the steps of:
1. Purified water is placed into a main vessel equipped with a stirrer.
2. The preservative i.e. (sodium benzoate, and/or ethylparaben, and/or Sodium metabisulfite and/or sodium propylparaben sodium) is added to the same vessel and mixed until completely dissolved.
3. Atomoxetine hydrochloride is added and mixed until completely dissolved.
4. The sweetener (glycerol and/or sucrose, and/or sucralose and/or xylitol and/or maltodextrin) is/are added and mixed until completely dissolved.
5. The flavors are added and mixed until they are completely dissolved.
6. Viscosity agent/complexation agents (SBE-β-CD and/or HPMC E15 and/or HPMC E3 and/or HPMC E6 and/or Starch paste and/or Pullulan) is/are added and mixed until complete dissolved.
7. The pH of the oral solution is adjusted to the desired value (pH 4-6.5)
8. The volume of the oral solution is adjusted to the desired batch volume by adding purified water The present invention also provides a method of making a pharmaceutical composition of oral solution by combining atomoxetine, water, preservatives, sweetener, flavors and complexation agent, and maintaining a pH in the range of 4 to 6.5 to form a solution. In one embodiment, the oral solution is an aqueous solution.

The pharmaceutical compositions in the form of oral atomoxetine solution in this disclosure successfully mask the bitterness of atomoxetine, while providing acceptable mouthfeel and aftertaste.

In addition to the improved taste, the oral solutions in this invention provide a stable shelf-life at room temperature of at least about 1-2 months, 2-4 months, 4-6 months, 6-8 months, 8-10 months, 10 months to 1 year. In one embodiment, the minimum level of the active ingredient that remains in solution at room temperature is >95%. No precipitation is observed after at least about 1 month.

5.3 Dosage and Unit Dosage Forms

In human therapeutics, the doctor will determine the posology which he considers most appropriate according to a preventive or curative treatment and according to the age, weight, degree of the disorder and other factors specific to the subject to be treated. In one embodiment, the disorder is ADHD. In certain embodiments, the present disclosed composition is used for the treatment of narcolepsy and depression. In some embodiments, the composition of the present disclosure is used for weight loss, treatment of eating disorder, addiction, cognitive dysfunction and anxiety disorder. In certain embodiments, doses are from about 5 to about 200 mg per day for an adult and children, or from about 10 to about 150 mg per day or from about 10 to 80 mg per day for an adult and children. In certain embodiments, doses are from about 5 to about 200 mg per day or 25 to 100 mg per day per adult and children. In certain embodiments, dose rates of from about 40 to about 200 mg per day are also contemplated.

In further aspects, provided are methods of treating a disorder in a subject by administering, to a subject in need thereof, an effective amount of a composition provided herein. The amount of the composition which will be effective in the treatment of a disorder or one or more symptoms thereof will vary with the nature and severity of the disorder. The frequency and dosage will also vary according to factors specific for each subject depending on the specific therapy (e.g., therapeutic agents) administered, the severity of the disorder, the route of administration, as well as age, body, weight, response, and the past medical history of the subject. In one embodiment, the disorder is ADHD.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.10 mg/kg and 3.00 mg/kg, or between 0.25 mg/kg and 2.0 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In one embodiment, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different degree of the disorder, as will be readily known by those of ordinary skill in the art. Similarly, amounts sufficient to manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the therapeutic effect of the composition or it may be decreased to reduce one or more side effects that a particular subject is experiencing.

In certain embodiment, the dosage of the composition provided herein administered to treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg. In certain embodiments, treatment can be initiated with one or more loading doses of a composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses. In certain embodiments, a dose of a composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL. In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same therapeutic agent may be repeated and the administration may be separated by at least at least 1 day, 2 days, 3 days, 5 days, 10 days, 15 days, 30 days, 45 days, 2 months, 75 days, 3 months, or 6 months. In certain aspects, provided herein are unit dosages comprising a composition, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art. In certain embodiments, dosages lower than those which have been or are currently being used to treat the disorder are used in combination with other therapies.

5.4 Patient Population

In one embodiment, a subject treated for a disorder in accordance with the methods provided herein is a human who has or is diagnosed with a disorder. In specific embodiments, the subject is diagnosed with a disorder that is treatable with administration of atomoxetine.

In another embodiment, a subject treated for a disorder in accordance with the methods provided herein is a human toddler. In another embodiment, a subject treated for ADHD in accordance with the methods provided herein is a human child. In another embodiment, a subject treated for a disorder in accordance with the methods provided herein is a human adult. In another embodiment, a subject treated for a disorder in accordance with the methods provided herein is a middle-aged human. In another embodiment, a subject treated for ADHD in accordance with the methods provided herein is an elderly human.

In some embodiments, a subject treated for a disorder in accordance with the methods provided herein that has recurring symptoms of a disorder.

In certain embodiments, a subject treated for a disorder in accordance with the methods provided herein is a human that is about 3 to about 6 years old, about 6 to 10 years old, about 10 to about 18 years old, about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old. In a specific embodiment, a subject treated for a disorder in accordance with the methods provided herein is a human that is 18 years old or older. In a particular embodiment, a subject treated for a disorder in accordance with the methods provided herein is a human child that is between the age of 6 year old to 18 years old. In a certain embodiment, a subject treated for a disorder in accordance with the methods provided herein is a human that is between the age of 12 years old and 18 years old. In a certain embodiment, the subject is a male human. In another embodiment, the subject is a female human.

In one embodiment, the patient is diagnosed with or have symptoms of ADHD.

In certain embodiments, the subject is Chinese, Japanese, Korean, Indian, Mexican, Brazilian, Turkish, Canadian, Spanish, Pakistani, Nigerian, Russian, Indonesian, German, Italian, French, Ukrainian, British, European or African.

5.5 Kits

Also provided are kits for use in methods of treatment for a disorder in accordance with the methods provided herein. The kits can include a pharmaceutical composition provided herein, a second composition, and instructions providing information to a health care provider regarding usage for treating the disorder. In one embodiment, the disorder is ADHD. Instructions may be provided in printed form or in the form of an electronic medium such as a floppy disc, CD, or DVD, or in the form of a website address where such instructions may be obtained. A unit dose of the therapeutic composition provided herein, or a second composition, can include a dosage such that when administered to a subject, a therapeutically or prophylactically effective plasma level of the composition can be maintained in the subject for at least 1 day. In some embodiments, a composition can be included as a sterile aqueous pharmaceutical composition. In some embodiments, suitable packaging is provided. As used herein, "packaging" includes a solid matrix or material customarily used in a system and capable of holding within fixed limits a composition provided herein suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

The kits described herein contain one or more containers, which contain the pharmaceutical composition as described. The kits also contain instructions for mixing, diluting, and/or administrating the compounds. The kits also include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions. In embodiments where liquid forms of the composition are used, the liquid form may be concentrated or ready to use. Suitable solvents for drug compositions are well known and are available in the literature. The solvent will depend on the composition and the mode of use or administration.

5.6 Method of Treatment

Provided herein is a method of treating a disorder by administering the pharmaceutical composition provided herein. The method comprises orally administering to a subject an effective amount of the disclosed pharmaceutical composition disclosed herein to reduce the symptoms of the disorder. Administration of the aqueous solutions of the present disclosure is achieved by introducing an appropriate volume of aqueous solution of atomoxetine in the mouth, which the patient then swallows. Alternatively, such solutions can be mixed with foods or beverages if preferred.

Atomoxetine is a norepinephrine reuptake inhibitor (NRI) that can prevent the reuptake of the neurotransmitter norepinephrine. The Norepinephrine Reuptake Inhibitors (NRIs) function primarily by inhibiting the reuptake of the neurotransmitter norepinephrine (noradrenaline) and/or epinephrine (adrenaline). Inhibiting the reuptake of norepinephrine elicits stimulating effects, thereby increasing both cortical arousal and energy levels. The NRI drugs are typically treatment for ADHD, narcolepsy, and depression. In some embodiments, the composition of the present disclosure is used for weight loss, eating disorders, treatment of addictions, cognitive dysfunction and treatment for certain anxiety disorders. In one embodiment, the disorder is ADHD.

6.0 EXAMPLES

The following examples illustrate the embodiments regarding synthesis and use of representative compositions provided herein. These examples are not intended, nor are they to be construed, as limiting the scope of the claimed subject matter. It will be clear that the scope of subject matter may be practiced otherwise than as particularly described herein. Numerous modifications and variations of the subject matter are possible in view of the teachings herein and, therefore, are within the scope the claimed subject matter.

6.1 Materials and Methods

6.1.1 Example 1

Atomoxetine Solution with Single Application of Flavor Agent

An oral aqueous atomoxetine solution according to the present disclosure is prepared by mixing the following ingredients in Table 1. All flavoring agents used in the present invention are commercially available.

TABLE 1

Atomoxetine Aqueous Solution Using Single Flavors

| Ingredient | Function | Formulation # | | | | | | | | | | | |
|---|---|---|---|---|---|---|---|---|---|---|---|---|---|
| | | 1 | 2 | 3 | 4 | 5 | 8 | 9 | 11 | 12 | 13 | 16 | 21 |
| | | % wt/wt | | | | | | | | | | | |
| Atomoxetine HCl | Active Ingredient | 1 | 1 | 1 | 1 | 1 | 1 | 1 | 1 | 1 | 1 | 1 | 1.14 |
| Glycerol | Sweetener | 2.5 | 2.5 | 2.5 | 2.5 | 2.5 | 5 | 7.5 | 7.5 | 7.5 | 7.5 | 7.5 | 7.5 |
| Sucrose | | 5.83 | 5.83 | 5.83 | 5.83 | 5.83 | 5.83 | 5.83 | 5.83 | 5.83 | 5.83 | 5.83 | 5.83 |
| Sucralose | | 0.83 | 0.83 | 0.83 | 0.83 | 0.83 | 0.83 | 0.83 | 0.83 | 0.83 | 0.83 | 0.83 | 0.83 |
| Xylitol | | — | — | — | — | — | — | — | — | — | — | — | — |
| Maltodextrin | | — | — | — | — | — | — | — | — | — | — | — | — |
| SBE-β-CD | Viscous agent/ complexation agents | 20.84 | 20.84 | 20.84 | 20.84 | 20.84 | 20.84 | 20.84 | 20.84 | 20.84 | 20.84 | 20.84 | 20.84 |
| Starch paste | | — | — | — | — | — | — | — | — | — | — | 1.5 | — |
| Pullulan | | — | — | — | — | — | — | — | — | — | — | — | 1 |
| Cherry | Flavor Agent | 1 | — | — | — | — | — | — | — | — | — | — | — |
| Raspberry | | — | — | — | — | — | — | — | — | — | — | — | — |
| Peppermint | | — | 1 | — | — | — | — | — | — | — | — | — | — |
| Strawberry | | — | — | 1 | — | — | — | — | — | — | — | — | — |
| Grape (Liquid) | | — | — | — | 1 | — | — | — | — | — | — | — | — |
| Grape (Powder) | | — | — | — | — | — | — | — | — | — | — | 0.5 | — |
| Banana | | — | — | — | — | 1 | 1 | 1 | — | — | — | — | — |
| Vanilla | | — | — | — | — | — | — | — | 1 | 0.25 | — | — | — |

TABLE 1-continued

Atomoxetine Aqueous Solution Using Single Flavors

| Ingredient | Function | 1 | 2 | 3 | 4 | 5 | 8 | 9 | 11 | 12 | 13 | 16 | 21 |
|---|---|---|---|---|---|---|---|---|---|---|---|---|---|
| | | | | | | | % wt/wt | | | | | | |
| Lime | | — | — | — | — | — | — | — | — | — | 0.3 | — | — |
| Passion Fruit | | — | — | — | — | — | — | — | — | — | — | — | 0.4 |
| Orange | | — | — | — | — | — | — | — | — | — | — | — | — |
| Water | solvent | | | | | | q.s. | | | | | | |

6.1.2 Example 2

Atomoxetine Solution with Binary Combination of Flavors

An oral aqueous atomoxetine solution according to the present disclosure is prepared by mixing the following ingredients in Table 2.

TABLE 2

Atomoxetine Aqueous Solution by Binary Combination of Flavors

| Ingredient | Function | 22 | 23 | 27 | 28 | 29 | 36 | 51 |
|---|---|---|---|---|---|---|---|---|
| | | | | | % wt/wt | | | |
| Atomoxetine HCl | Active Ingredient | 1.14 | 1.14 | 1.482 | 1.482 | 1.482 | 1.482 | 1.482 |
| Glycerol | Sweetener | 7.5 | 7.5 | 7.5 | 7.5 | 7.5 | 7.5 | 7.5 |
| Sucrose | | 5.83 | 5.83 | 5.83 | 5.83 | 7.58 | 7.58 | 7.58 |
| Sucralose | | 0.83 | 0.83 | 0.83 | 0.83 | 1.08 | 1.08 | 1.08 |
| SBE-β-CD | Viscous agent/ complexation agents | 20.84 | 20.84 | 20.84 | 20.84 | 27.09 | 27.09 | 27.09 |
| HPMC E6 | | — | — | — | 1 | 1 | — | — |
| Pullulan | | 1 | 1 | 1 | 1 | 1 | 2 | 1 |
| Peppermint | Flavor Agent | 0.1 | 0.15 | 0.05 | 0.05 | 0.05 | 0.05 | 0.15 |
| Strawberry | | — | — | — | — | — | 1.482 | — |
| Passion Fruit | | 0.4 | 0.4 | 0.4 | 0.4 | 0.4 | — | — |
| Orange | | — | — | — | — | — | — | 0.5 |
| Water | Solvent | | | | q.s. | | | |

6.1.4 Example 3

Atomoxetine Solution with Peppermint Flavor, Orange Flavor and Pullulan

An oral aqueous atomoxetine solution according to the present disclosure is prepared by mixing the following ingredients in Table 3.

TABLE 3

Atomoxetine Aqueous Solution by Binary Combination of Flavors and Viscosity Agent.

| Ingredient | Function | 51 | 56 | 57 | 58 | 59 |
|---|---|---|---|---|---|---|
| | | | | % wt./wt | | |
| Atomoxetine HCl | Active Ingredient | 1.482 | 1.482 | 1.482 | 0.593 | 0.593 |
| Glycerol | Sweetener | 7.5 | 7.5 | 7.5 | 7.5 | 7.5 |
| Sucrose | | 7.58 | 7.58 | 7.58 | 7.58 | 7.58 |
| Sucralose | | 1.08 | 1.08 | 1.08 | 1.08 | 1.08 |
| SBE-β-CD | Viscous agent/ complexation agents | 27.09 | 27.09 | 27.09 | 27.09 | 27.09 |
| Pullulan | | 1 | 1 | 1 | 1 | 1 |
| Peppermint | Flavor Agent | 0.15 | 0.15 | 0.15 | 0.15 | 0.15 |
| Orange | | 0.5 | 0.5 | 0.5 | 0.5 | 0.5 |
| Sodium metabisulfite | Preservatives | — | 0.005 | 0.005 | — | 0.005 |
| propyl paraben (sodium) | | — | 0.02 | 0.02 | 0.02 | 0.02 |
| 8.5% Phosphoric acid | pH adjust Agent/ Buffer Agent | — | — | Adjust to pH 5.5 | | |
| Water | Solvent | | | q.s. | | |

6.2 Taste Study

In this taste study, the flavor test results are based on the analysis of a panel of 4-5 highly trained judges who are experienced in detailed flavor analysis. The test results are illustrated in the following Table 4.

The evaluation was performed by classifying bitterness taste, numbness and after taste into the following three classes: Level 3: Strong bitter taste, strong numbness taste is sensed and strong after taste—Level 2: Some bitter taste, some numbness taste is sensed and some after taste—Level 1: No bitter taste, no numbness taste is sensed and no after mouth taste.

| Formulation # | Bitterness Score | Numbness Score | After taste Score |
|---|---|---|---|
| 1 | 3 | 1 | 3 |
| 2 | 2 | 1 | 2 |
| 3 | 2 | 1 | 2 |
| 4 | 3 | 1 | 2 |
| 5 | 2 | 1 | 2 |
| 8 | 2 | 1 | 1 |
| 9 | 2 | 1 | 1 |
| 11 | 2 | 1 | 3 |
| 12 | 2 | 1 | 3 |
| 13 | 2 | 1 | 3 |
| 16 | 3 | 1 | 1 |
| 21 | 2 | 1 | 2 |
| 22 | 2 | 1 | 1 |
| 23 | 2 | 1 | 1 |
| 27 | 2 | 1 | 1 |
| 28 | 2 | 1 | 1 |
| 29 | 2 | 1 | 1 |
| 36 | 2 | 1 | 1 |
| 51 | 1 | 1 | 1 |
| 56 | 1 | 1 | 1 |
| 57 | 1 | 1 | 1 |
| 58 | 1 | 1 | 1 |
| 59 | 1 | 1 | 1 |

The analysis results in Table 4 illustrate the effectiveness of different flavoring agents in the masking of the potent bitterness. The samples are prepared with essentially the same method except the addition of different flavoring agents.

The atomoxetine solution with Peppermint Flavor and pullulan in Example 4 provides the most preferable taste comparing with peppermint flavored (Example 1), orange flavored (Example 2) atomoxetine solutions.

The bitter-masking agents do not interfere with the effectiveness of the flavoring and sweetening agents in improving the taste of atomoxetine solutions, and none of these components adversely affects the medicinal effectiveness of atomoxetine. Such palatable atomoxetine formulations are useful in improving patient compliance in pediatric and other populations being treated for a disorder. In one embodiment, the disorder is ADHD.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

Exemplary Systems and Methods are Set Out in the Following Items:

Item 1. A pharmaceutical composition comprising: (i) 0.5 mg/ml to 25 mg/ml of atomoxetine, and (ii) a carrier comprising: 0.01 mg/ml to 5 mg/ml peppermint flavor, 0.01 mg/ml to 10 mg/ml orange flavor, and 0.5 mg/ml to 600 mg/ml one or more sweeteners, wherein the pharmaceutical composition is a homogeneous oral solution, and wherein the pH of the composition is from 4 to 6.5. In one embodiment, the pH of the composition is from 6.1-6.5. In one embodiment, the pH of the composition is 5.5. In one embodiment, the composition does not contain raspberry flavor.

Item 2. The pharmaceutical composition of item 1, wherein the atomoxetine is atomoxetine hydrochloride.

Item 3. The pharmaceutical composition of anyone of the above items, wherein the solution is an aqueous solution.

Item 4. The pharmaceutical composition of anyone of the above items, wherein the concentration of atomoxetine is from 0.5 mg/ml to 25 mg/ml.

Item 5. The pharmaceutical composition anyone of the above items, further comprising 1 mg/ml to 300 mg/ml viscosity agent.

Item 6. The pharmaceutical composition anyone of the above items, wherein the viscosity agent is pullulan. HPMC E15, HPMC E3. HPMC E6. SBE-β-CD, or a combination thereof.

Item 7. The pharmaceutical composition anyone of the above items, wherein the ratio of the peppermint flavor to orange flavor to sweetener is 1:3:100.

Item 8. The pharmaceutical composition of anyone of the above items, wherein the sweetener is sucralose or sucrose or a combination thereof.

Item 9. The pharmaceutical composition anyone of the above items, wherein the concentration of the peppermint flavor is from 0.01 mg/ml to 5 mg/ml.

Item 10. The pharmaceutical composition anyone of the above items, wherein the concentration of the orange flavor is from 0.01 mg/ml to 10 mg/ml.

Item 11. The pharmaceutical composition of anyone of the above items, wherein the pH is from 4 to 6.5.

Item 12. The pharmaceutical composition anyone of the above items, which is free of ethanol, sorbitol, and mannitol.

Item 13. The pharmaceutical composition of anyone of the above items, further comprising glycerol and sulfobutylether-cyclodextrin ("SBE-β-CD").

Item 14. A pharmaceutical composition which consists essentially of:
- 1-10 mg/ml atomoxetine hydrochloride,
- 50-100 mg/ml glycerol,
- 50-100 mg/ml sweeteners,
- 200-300 mg/ml SBE-β-CD,
- 0.2-5 mg/ml peppermint flavor,
- 0.1-10 mg/ml orange flavor, and
- 0.5-10 mg/ml pullulan, and wherein the pH of the composition is from 4 to 6.5.

Item 15. A method for treating a disorder comprising orally administering to a subject an effective amount of the pharmaceutical composition of any one of the above items.

Item 16. The method of items 15 wherein the disorder is attention deficit hyperactivity disorder ("ADHD"), narcolepsy, depression, obesity, eating disorder, addiction, cognitive dysfunction and anxiety disorder.

Item 17. The method of items 15-16 wherein the disorder is ADHD.

Item 18. The method of items 15-17, wherein the subject is a human.

Item 19. The method of item 15-18 wherein the human is a child or an elderly.

What is claimed is:

1. A pharmaceutical composition comprising: (i) about 0.5 mg/ml to about 25 mg/ml of atomoxetine or a pharmaceutically acceptable salt thereof, and (ii) a carrier comprising: about 0.01 mg/ml to about 5 mg/ml peppermint flavor, about 0.01 mg/ml to about 10 mg/ml orange flavor, and about 0.5 mg/ml to about 600 mg/ml one or more sweeteners, wherein the pharmaceutical composition is a homogeneous oral solution, wherein the pharmaceutical composition is free of xylitol and maltitol, and wherein the pH of the composition is from about 4 to about 6.6.

2. The pharmaceutical composition of claim 1, wherein the atomoxetine is atomoxetine hydrochloride.

3. The pharmaceutical composition of claim 1, wherein the solution is an aqueous solution.

4. The pharmaceutical composition of claim 1, wherein the concentration of atomoxetine is from about 1 mg/ml to about 10 mg/ml.

5. The pharmaceutical composition of claim 1, further comprising about 1 mg/ml to about 300 mg/ml viscosity agent.

6. The pharmaceutical composition of claim 5, wherein the viscosity agent is pullulan, HPMC E15, HPMC E3, HPMC E6, SBE-β-CD, or a combination thereof.

7. The pharmaceutical composition of claim 1, wherein the ratio of the peppermint flavor to orange flavor to sweetener is about 1:3:100.

8. The pharmaceutical composition of claim 1, wherein the sweetener is sucralose, sucrose or a combination thereof.

9. The pharmaceutical composition of claim 1, wherein the concentration of the peppermint flavor is from about 0.2 mg/ml to about 5 mg/ml.

10. The pharmaceutical composition of claim 1, wherein the concentration of the orange flavor is from about 0.1 mg/ml to about 10 mg/ml.

11. The pharmaceutical composition of claim 1, wherein the pH is from about 4 to about 5.

12. The pharmaceutical composition of claim 1, which is free of ethanol, sorbitol, and mannitol.

13. The pharmaceutical composition of claim 1, wherein the composition does not comprise raspberry flavor.

14. A pharmaceutical composition which consists essentially of:
about 1 mg/ml-about 10 mg/ml atomoxetine hydrochloride,
about 50 mg/ml-about 100 mg/ml glycerol,
about 50 mg/ml-about 100 mg/ml sweeteners,
about 0.2 mg/ml-about 5 mg/ml peppermint flavor,
about 0.1 mg/ml-about 10 mg/ml orange flavor, and
wherein the pH of the composition is from about 4 to about 6.6.

15. A method for treating a disorder in a subject comprising orally administering to the subject an effective amount of the pharmaceutical composition of claim 1 wherein the disorder is attention deficit hyperactivity disorder ("ADHD"), narcolepsy, depression, obesity, eating disorder, addiction, cognitive dysfunction or anxiety disorder.

16. The method of claim 15 wherein the disorder is ADHD.

17. The method of claim 15, wherein the subject is a human.

18. The method of claim 15, wherein the human is a child or an elderly.

* * * * *